US006060808A

United States Patent [19]

Cassady et al.

[11] Patent Number: 6,060,808

[45] Date of Patent: May 9, 2000

[54] TRANSLUCENT PERSONAL CLEANSING BARS

[75] Inventors: Timothy J. Cassady, Hamilton; Robert R. Schoettker, Cincinnati, both of Ohio

[73] Assignee: Henkel Corporation, Gulph Mills, Pa.

[21] Appl. No.: 09/150,536

[22] Filed: Sep. 9, 1998

Related U.S. Application Data

[60] Provisional application No. 60/085,322, May 13, 1998.

[51] Int. Cl.$^7$ .............................. A61K 7/50; C11D 17/00

[52] U.S. Cl. ........................... 310/147; 510/152; 510/155

[58] Field of Search .................................... 510/147, 152, 510/155, 141

[56] References Cited

U.S. PATENT DOCUMENTS

| | | | |
|---|---|---|---|
| 5,312,559 | 5/1994 | Kacher et al. | 252/125 |
| 5,409,640 | 4/1995 | Giret et al. | 252/546 |
| 5,449,763 | 9/1995 | Wulff et al. | 536/18.6 |
| 5,750,663 | 5/1998 | Gross et al. | 536/4.1 |

FOREIGN PATENT DOCUMENTS

| | | |
|---|---|---|
| 0 463 912 A1 | 1/1992 | European Pat. Off. . |

*Primary Examiner*—Necholus Ogden
*Attorney, Agent, or Firm*—John E. Drach; Steven J. Trzaska

[57] ABSTRACT

A translucent personal cleansing bar containing: (a) an alkyl polyglycoside of formula I:

$$R_1O(Z)_a \qquad (I)$$

wherein $R_1$ is a monovalent organic radical having from about 8 to 10 carbon atoms, and a is a number having a value of from about 1.40 to 1.55; (b) a soap component; and (c) water.

16 Claims, No Drawings

TRANSLUCENT PERSONAL CLEANSING BARS

CROSS-REFERENCE TO RELATED APPLICATIONS

This application claims the benefit of earlier filed and copending provisional application Ser. No. 60/085,322, filed on May 13, 1998, the entire contents of which are incorporated herein by reference.

STATEMENT REGARDING FEDERALLY SPONSORED RESEARCH OR DEVELOPMENT

NOT APPLICABLE.

BACKGROUND OF THE INVENTION

The present invention generally relates to translucent personal cleansing bars, and a method for making same. More particularly, the invention relates to a translucent soap bar having enhanced lather and tactile properties.

Soaps made from mixtures of animal fats and vegetable oils have been made for many years. Today, the majority of personal cleansing/soap bars are made from a mixture of tallow and coconut oil or from the fatty acids obtained from such oils. Such products have, for the most part, been accepted by consumers, although improvements in certain of their properties are constantly being sought.

Aside from improvements in the cleaning, lathering and rinsing properties of personal cleansing bars, the aesthetic appearance of these bars has also grown to be increasingly important to consumers. There is a general consensus among today s consumers that a clear, i.e., less opaque personal cleansing bar is more desirable than a conventional opaque bar. The reasons for this may stem from the consumers belief that such bars are somehow more natural or contain fewer undesirable constituents or that a translucent or transparent soap bar contains ingredients that are more easily rinsed from the skin after washing. Regardless of the reasons for this belief, in an effort to appease consumers desires, manufacturers have begun making transparent and translucent personal cleansing bars.

Transparent soap bars depend for their distinctive appearance upon the fact that the soap has an ultramicrocrystalline form. The incorporation of glycerol and sugars also tend to cause soap to assume this form. The effect is entirely physical, and depends upon the conditions under which the soap crystallizes rather than the presence of alcohol or any other substance in the finished soap cake. Thus, a transparent soap made with the aid of alcohol retains its appearance after most of the alcohol has been evaporated from it.

Transparent soaps vary greatly in composition. They may be prepared simply by dissolving soap flakes in alcohol and then driving off the greater part of the alcohol. Such a product will not be greatly different in composition from the original soap flakes. A more usual method of manufacture, however, is to add alcohol and glycerol, in the proportion of about two parts of alcohol to one of glycerol, to a hot saponified batch of semi-boiled soap until a rapidly cooled sample is clear, after which the batch is framed in the usual way. Sugar may also be added. The fats used in transparent soaps usually are tallow and coconut oil. Up to about 30% castor oil is often used in the fat charge, as the presence of this oil reduces the amount of alcohol, glycerol or sugar required to render the soap transparent. The anhydrous soap content of transparent soaps is usually well under 50%. A soap bar is deemed to be transparent when 12 pt type is readable through a one inch thick bar.

Soap translucency is quantified using the contrast ratio method for measuring opacity. The opacity value gives an inverse measurement of translucency. According to this method, a ⅝ inch (16 mm) thick personal cleansing bar, which is flat on two parallel faces, is first formed. A Pacific Scientific Colorgard System/05 Colorimeter, similar to a Hunter Tristimulus Colorimeter) is then calibrated and used to obtain two measurements. The first measurement is taken with the translucent bar backed by a white tile, placed over a light source, to achieve maximum reflectance of the light which passes through the sample. The second measurement is then taken with the translucent bar backed by a black tile, placed over a light source, for minimum reflectance of light through the sample. The percent opacity is then defined as the value of the second measurement divided by the first measurement multiplied by one hundred.

Thus, a transparent soap bar has a percent opacity for a ⅝ inch to ¾ inch thick bar of less than 40 percent. A typical value of 20 to 35 percent opacity is often achieved.

Translucent bars, on the other hand, are not as clear as transparent bars, i.e., they possess a higher degree of opacity than that of a transparent bar. A bar is deemed to be translucent when its percent opacity is from 40 to 85%. Similarly, a bar is deemed to be opaque when its percent opacity is greater than 85%.

BRIEF SUMMARY OF THE INVENTION

The present invention is directed to a solid translucent personal cleansing composition containing:

(a) an alkyl polyglycoside corresponding to formula I:

$$R_1O(Z)_a \quad (I)$$

wherein $R_1$ is a monovalent organic radical having from about 8 to 10 carbon atoms, and a is a number having a value of from about 1.40 to 1.55;

(b) a soap component derived from a fatty acid having an iodine value of from about 25 to about 44; and (c) water.

The present invention is also directed to a process for making a solid translucent personal cleansing composition involving the steps of:

(a) providing a soap component derived from a fatty acid having an iodine value of from about 25 to about 44;

(b) providing an alkyl polyglycoside corresponding to formula I:

$$R_1O(Z)_a \quad (I)$$

wherein $R_1$ is a monovalent organic radical having from about 8 to 10 carbon atoms, and a is a number having a value of from about 1.40 to 1.55;

(c) providing a water component;

(d) mixing (a)–(c), at a temperature of from about 60 to about 95° C., to form a liquid personal cleansing composition; and (e) transforming the liquid personal cleansing composition into a solid form.

BRIEF DESCRIPTION OF THE SEVERAL VIEWS OF THE DRAWING

NOT APPLICABLE.

DETAILED DESCRIPTION OF THE INVENTION

Other than in the operating examples, or where otherwise indicated, all numbers expressing quantities of ingredients or reaction conditions used herein are to be understood as being modified in all instances by the term "about".

The solid translucent personal cleansing composition of the present invention is generally comprised of: (1) an alkyl polyglycoside corresponding to formula I:

$$R_1O(Z)_a \quad (I)$$

wherein $R_1$ is a monovalent organic radical having from about 8 to 10 carbon atoms, and a is a number having a value of from about 1.40 to 1.55; (2) a soap component derived from a fatty acid having an iodine value of from about 25 to about 44 which consists of a fatty acid which is at least 95% neutralized by sodium hydroxide; and (3) water.

The alkyl polyglycoside employed in the present invention corresponds to formula I:

$$R_1O(Z)_a \quad (I)$$

wherein $R_1$ is a monovalent organic radical having from about 8 to 10 carbon atoms, and a is a number having a value of from about 1.40 to 1.55. Such an alkyl polyglycoside is commercially available from Henkel Corporation, Emery Division, under the tradename GLUCOPONO 220 UP.

The soap component of the personal cleansing bars according to the invention can be any saturated or unsaturated, branched or linear carboxylic acid ("fatty acid") having from 8 to 30 carbon atoms or a mixture of such acids. In a preferred embodiment of the personal cleansing composition according to the invention, the soap component is a mixture of soaps of fatty acids comprised of 80–85% by weight of the sodium soap of a typical commercial grade partially hydrogenated tallow fatty acid having an iodine value of from about 30 to about 45, a titer value of from about 40–55 and an AV value of from about 190–210, and from about 15–20% by weight of a typical commercial grade coconut fatty acid. An example of a typical commercial grade partially hydrogenated tallow fatty acid is EMERY® 401 Modified Fatty Acid, a trademark product of Henkel Corporation, Chemical Group, Cincinnati, Ohio which has a typical acid value of 199–208, iodine value of 34–44 and titer of 44–53.

An example of a typical commercial grade coconut fatty acid is EMERY®625 Partially Hydrogenated Coconut Fatty Acid, a trademark product of Henkel Corporation, Chemical Group, Cincinnati, Ohio, which has an average weight percent composition of 49% lauric acid, 19% myristic acid, 9% palmitic acid, 7% stearic acid, 7% caprylic acid, 6% capric acid, and 3% oleic acid.

The preferred degree of neutralization of the fatty acids can range from 95% to 105% with the most preferred range being 99–101%. The fatty acids can be neutralized by bases such as alkali metal hydroxides such as sodium hydroxide. Coconut fatty acid can be added to the neat soap to react with any excess sodium hydroxide in order to eliminate excess alkalinity in the formulation.

It should be noted that regardless of which type of soap component is employed, it is imperative that the soap component be derived from a fatty acid having an iodine value of from about 25 to about 44, and preferably from about 31 to about 37.

Another component which may also be employed, if desired, in order to formulate the translucent personal cleansing composition of the present invention is a polyol component.

The polyol component of the soap bars according to the invention can be any aliphatic compound having 2 or more alcohol functionalities. Such polyols include diols, triols, tetraols, etc. Examples of such polyols include, but are not limited to, ethylene glycol, 1,2-propylene glycol, 1,3-propylene glycol, diethylene glycol, dipropylene glycol, triethylene glycol, polyethylene glycol, 1,6-hexylene glycol, glycerine, polyglycerols, monosaccharides such as glucose or fructose, disaccharides such as sucrose, sorbitol, polydextrose and polyvinyl alcohol. Preferred polyols include 1,2-propylene glycol, glycerine, polyglycerol, polydextrose and sorbitol. The most preferred polyol is glycerine.

According to one embodiment of the present invention, there is provided a translucent personal cleansing composition which can readily be made into a solid bar using conventional soapmaking/bar finishing equipment, the personal cleansing composition containing: (a) from about 1 to about 19% by weight, and preferably from about 6 to about 10% by weight, of the alkyl polyglycoside of formula I; (b) from about 52 to about 84% by weight, and preferably from about 67 to about 81% by weight, of the soap component; optionally, (c) up to about 12% by weight, and preferably from about 3 to about 8% by weight, of a polyol component, preferably glycerine; and (d) remainder, to 100%, water, all weights being based on the total weight of the solid composition.

According to another embodiment of the present invention, there is also provided a process for making a solid translucent personal cleansing composition. The process involves adding the alkyl polyglycoside of formula I to the soap component, in the above-disclosed proportions.

With respect to the soap component, either a neat soap solution having a moisture content of from about 20 to about 35%, and preferably about 30%, may be used or the soap component may be formed in situ during the formulation of the liquid personal cleansing composition.

In the event that a neat soap solution is employed, the alkyl polyglycoside of formula I is added to the neat soap at a temperature of from about 60 to about 95° C., and preferably about 60° C. It is imperative that, when using a neat soap solution as the soap component to formulate the personal cleansing bar of the invention, the alkyl polyglycoside is added to the neat soap component at both a temperature ranging from about 60 to about 95° C., and preferably at about 60° C., and at a point prior to the neat soap being dried down, i.e., prior to its entering the heat exchanger which is in front of the vacuum dryer used to reduce moisture to a processable level in a conventional soap processing plant, in order to obtain a personal cleansing bar that is translucent.

On the other hand, when the soap component is formed in situ, a fatty acid, fat, oil or a mixture thereof is combined with a caustic component, such as sodium or potassium hydroxide, the alkyl polyglycoside of formula I, water and, optionally, a glycerine component. By combining these components at a temperature ranging from about 60 to about 95° C., the soap component is formed in situ, along with the liquid personal cleansing composition. It should be noted that the liquid personal cleansing composition, once formulated, is not translucent in appearance. It is only after it is transformed into a bar that it becomes translucent.

The transformation of the liquid personal cleansing composition into a translucent bar involves the use of conventional refining, plodding and stamping processes. It is the presence of the alkyl polyglycoside of formula I which improves the processing of the translucent personal cleansing bars by enabling translucency to be maintained over a wide range of moisture levels, i.e., from about 5 to about 17% moisture in the finished bar. Translucency can be achieved by refining the liquid personal cleansing composition using refining plodders equipped with 10, 20 and 30 mesh screens. The presence of the alkyl polyglycoside eliminates the need to employ roll mills to form translucent bars. Moreover, translucent soap formulations are typically processed at a moisture content of from 15–17%. If a conventional liquid personal cleansing composition were to be refined at a moisture content below 15%, the translucency of the finished bar would be adversely affected. The presence of the alkyl polyglycoside allows the formulation to be processed at a substantially lower moisture level, i.e., 6–17% while maintaining translucency.

It should also be noted that other additives which are not detrimental to the translucency of the composition, which are typically used in formulating personal cleansing bars, may also be employed without departing from the spirit of the invention.

The present invention will be better understood from the examples which follow, all of which are meant to be illustrative only, and are not intended to unduly limit the scope of the invention.

EXAMPLE 1

A translucent personal cleansing bar in accordance with the present invention was formed using an 85/15 sodium tallowate/sodium cocoate soap and having the following formulation:

| Component | %/wt. |
|---|---|
| (a) sodium partially hydrogenated tallowate | 68.76 |
| (b) sodium cocoate | 12.13 |
| (c) GLUCOPON ® 220 UP | 8.99 |
| (d) water | 10.12 |
| | 100.00 |

The degree of translucency of Example 1 was determined using the contrast ratio method previously described. The percent opacity was measured at 70%.

EXAMPLE 2

| Component | %/wt. |
|---|---|
| (a) sodium partially hydrogenated tallowate | 60.33 |
| (b) sodium cocoate | 10.65 |
| (c) GLUCOPON ® 220 UP | 8.50 |
| (d) glycerine | 5.10 |
| (e) sodium chloride | 0.43 |
| (f) water | 15.00 |
| | 100.00 |

The percent opacity of the bar of Example 2 was measured at 64%.

EXAMPLE 3

A translucent personal cleansing bar was prepared using a 60/20/20 palm stearine acids soap/palm acids soap/coconut fatty acid soap having the following formulation:

| Component | %/wt. |
|---|---|
| (a) sodium palm stearinate | 42.58 |
| (b) sodium palmate | 14.19 |
| (c) sodium cocoate | 14.19 |
| (d) GLUCOPON ® 220 UP | 8.50 |
| (e) glycerine | 5.10 |
| (f) sodium chloride | 0.43 |
| (g) water | 15.00 |
| | 100.00 |

The percent opacity of the bar was measured at 75%.

Comparative Example 1

A comparative personal cleansing bar was formed using an alkyl polyglycoside different from the one disclosed by the present invention, having the following formulation:

Comparative Example

| Component | %/wt. |
|---|---|
| (a) GLUCOPON ® 325* | 8.99 |
| (b) sodium partially hydrogenated tallowate | 68.76 |
| (c) sodium cocoate | 12.13 |
| (d) water | 10.12 |
| | 100.00 |

(*)GLUCOPON ® 325 Surfactant is an alkyl polyglycoside in which the alkyl group contains 9 to 11 carbon atoms and having an average degree of polymerization of 1.5.

The degree of translucency of this bar was measured at 97% which indicates that it is opaque.

What is claimed is:

1. A translucent personal cleansing bar comprising:

(a) from about 1 to about 19% by weight of an alkyl polyglycoside corresponding to formula I:

$$R_1O(Z)_a \quad \text{(I)}$$

wherein $R_1$ is a monovalent organic radical having from about 8 to 10 carbon atoms, and a is a number having a value of from about 1.40 to 1.55;

(b) from about 52 to about 84% by weight of a soap component derived from a fatty acid having an iodine value from about 25 to about 44; and (c) from about 6 to about 20% by weight of water.

2. The bar of claim 1 wherein the soap component consists of from about 80 to about 85% by weight of a partially hydrogenated tallow fatty acid soap and from about 15 to about 20% by weight of a coconut fatty acid soap.

3. The bar of claim 1 further comprising a polyol component.

4. The bar of claim 3 wherein the polyol component is glycerine.

5. The bar of claim 3 wherein the polyol component is present in the bar in an amount of up to about 12% by weight, based on the weight of the bar.

6. A translucent personal cleansing bar comprising:

(a) from about 3 to about 10% by weight of an alkyl polyglycoside of formula I:

$$R_1O(Z)_a \quad \text{(I)}$$

wherein $R_1$ is a monovalent organic radical having from about 8 to 10 carbon atoms, and a is a number having a value of from about 1.40 to 1.55;

(b) from about 67 to about 81% by weight of a soap component derived from a fatty acid having an iodine value of from about 31 to about 39;

(c) from about 3 to about 8% by weight of glycerine; and (d) remainder, water, all weights being based on the weight of the bar.

7. The bar of claim 6 wherein the bar has a moisture content of from about 6 to about 15% by weight, based on the weight of the bar.

8. A process for making a translucent personal cleansing bar comprising:

(a) from about 52 to about 84% by weight of providing a soap component derived from a fatty acid having an iodine value of from about 25 to about 44;

(b) from about 1 to about 19% by weight of providing an alkyl polyglycoside corresponding to formula I:

$$R_1O(Z)_a \quad (I)$$

wherein $R_1$ is a monovalent organic radical having from about 8 to 10 carbon atoms, and a is a number having a value of from about 1.40 to 1.55;

(c) providing from about 20 to about 35% by weight of water;

(d) mixing (a)–(c), at a temperature of from about 60 to about 95° C., to form a liquid personal cleansing composition; and (e) transforming the liquid personal cleansing composition into a solid bar.

9. The process of claim 8 wherein the neat soap solution consists of from about 39 to about 76% by weight of a partially hydrogenated tallow fatty acid soap and from about 3 to about 32% by weight of a coconut fatty acid soap.

10. The process of claim 8 wherein the soap component is formed in situ, during the formulation of the liquid personal cleansing composition.

11. The process of claim 10 wherein the soap component is formed by reacting a fat, oil, fatty acid or mixture thereof with a caustic component.

12. The process of claim 8 wherein the composition further contains a polyol component.

13. The process of claim 12 wherein the polyol component is glycerin.

14. The process of claim 12 wherein the polyol component is present in the composition in an amount of up to about 12% by weight.

15. A process for making a translucent personal cleansing bar comprising:

(a) providing from about 67 to about 81% by weight of a soap component derived from a fatty acid having an iodine value of from about 31 to about 39;

(b) providing from about 6 to about 10% by weight of an alkyl polyglycoside of formula I:

$$R_1O(Z)_a \quad (I)$$

wherein $R_1$ is a monovalent organic radical having from about 8 to 10 carbon atoms, and a is a number having a value of from about 1.40 to 1.55;

(c) providing from about 3 to about 8% by weight of glycerine;

(d) providing remainder, to 100%, water;

(e) mixing (a)–(c), at a temperature of from about 60 to about 95° C., to form a translucent personal cleansing composition; and (f) transforming the liquid personal cleansing composition into a solid translucent bar.

16. The process of claim 15 wherein the bar has a moisture content of from about 6 to about 15% by weight, based on the weight of the bar.

* * * * *